United States Patent
Coggins et al.

(10) Patent No.: US 8,662,347 B2
(45) Date of Patent: Mar. 4, 2014

(54) MEDICAL ELECTRODE DISPENSERS

(75) Inventors: Scott Coggins, Littleton, MA (US); Rachel Starr, Randolph, MA (US); Scott Holmes, Franklin, MA (US); Steve T. Wilson, Brockville (CA); David R. Swisher, St. Charles, MO (US); David T. Middleton, Jr., Skaneateles, NY (US); Michael W. Konieczny, Skaneateles, NY (US); Robert L. Naas, Skaneateles, NY (US); Paul Eric Carlson, Skaneateles, NY (US)

(73) Assignee: Covidien LP, Mansfield, MA (US)

( * ) Notice: Subject to any disclaimer, the term of this patent is extended or adjusted under 35 U.S.C. 154(b) by 96 days.

(21) Appl. No.: 13/248,500

(22) Filed: Sep. 29, 2011

(65) Prior Publication Data

US 2012/0193372 A1 Aug. 2, 2012

Related U.S. Application Data

(60) Provisional application No. 61/387,632, filed on Sep. 29, 2010.

(51) Int. Cl.
*B65H 5/28* (2006.01)
(52) U.S. Cl.
USPC .................................. 221/71; 221/70; 221/73
(58) Field of Classification Search
USPC ............................ 221/70, 71, 72, 73, 74, 268
See application file for complete search history.

(56) References Cited

U.S. PATENT DOCUMENTS

| | | | |
|---|---|---|---|
| 1,026,778 A | 5/1912 | Toles | |
| 2,600,904 A | 6/1952 | Morgan | |
| 2,943,628 A * | 7/1960 | Howell | 600/391 |
| 3,530,494 A | 9/1970 | Baratta | |
| 3,674,176 A * | 7/1972 | Sagi | 221/70 |
| 4,090,752 A * | 5/1978 | Long | 312/42 |
| 4,339,035 A | 7/1982 | Marcus et al. | |
| 4,393,584 A | 7/1983 | Bare et al. | |
| 4,543,958 A * | 10/1985 | Cartmell | 221/32 |
| 4,566,606 A | 1/1986 | Kling | |
| 4,584,962 A | 4/1986 | Cartmell | |
| 4,838,273 A * | 6/1989 | Cartmell | 600/385 |
| 4,954,210 A * | 9/1990 | Desmond | 221/71 |
| 5,154,335 A | 10/1992 | Bredow et al. | |
| 5,178,144 A | 1/1993 | Cartmell | |
| 5,191,887 A | 3/1993 | Cartmell | |
| 2009/0155594 A1 | 6/2009 | Evans et al. | |

* cited by examiner

*Primary Examiner* — Timothy Waggoner
(74) *Attorney, Agent, or Firm* — Lisa E. Winsor, Esq.

(57) ABSTRACT

A medical dispenser for storing and dispensing electrodes includes a housing having a front member and a back member, at least one electrode strip disposed between the front member and the back member of the housing and an actuator mounted to the front member of the housing and adapted to engage the at least one electrode strip. The electrode strip includes a strip member and a plurality of electrodes mounted to the strip member. The actuator is movable relative to the front member such that movement of the actuator results in corresponding movement of the at least one electrode strip to dispense an electrode from the housing. The actuator may be adapted to engage an electrode of the at least one electrode strip. In one embodiment, the actuator is adapted to engage a male terminal of the electrode.

19 Claims, 15 Drawing Sheets

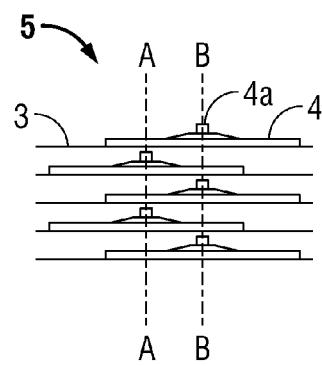
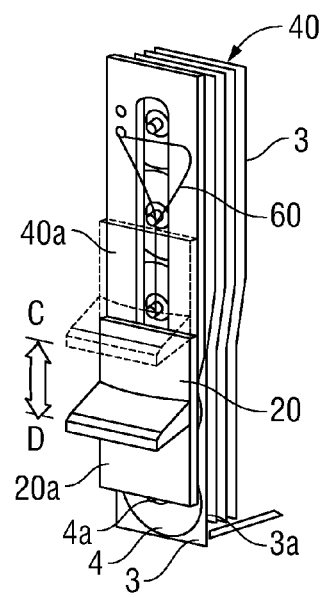
FIG. 5  FIG. 6
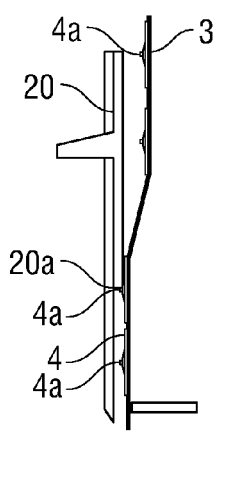
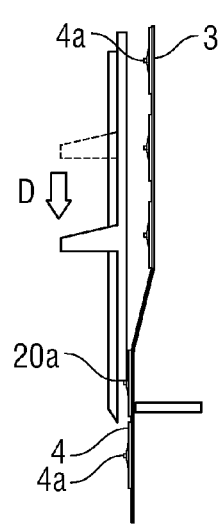
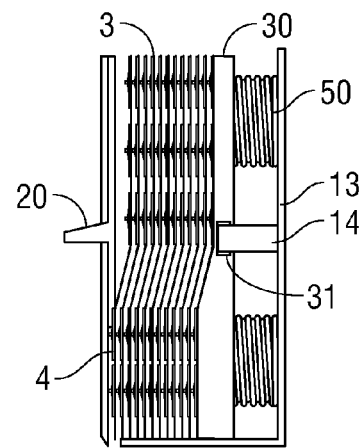
FIG. 7A  FIG. 7B  FIG. 8

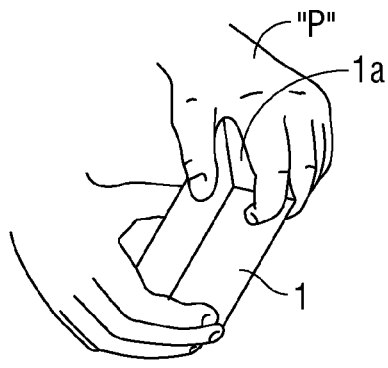
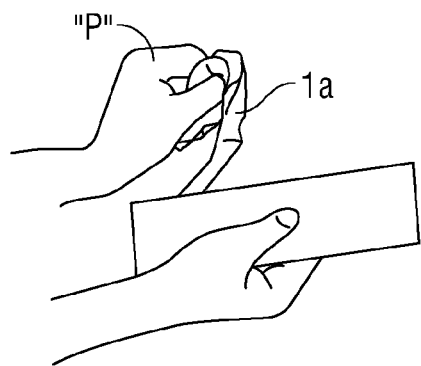
FIG. 9
FIG. 10A
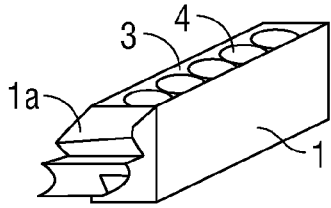
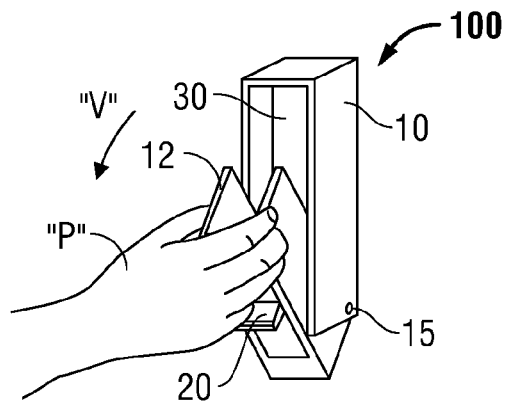
FIG. 10B
FIG. 11
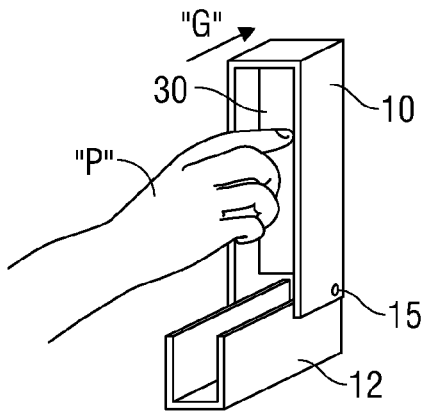
FIG. 12

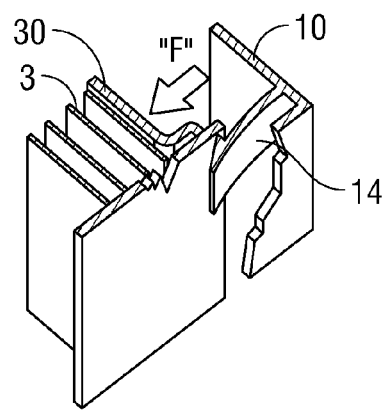
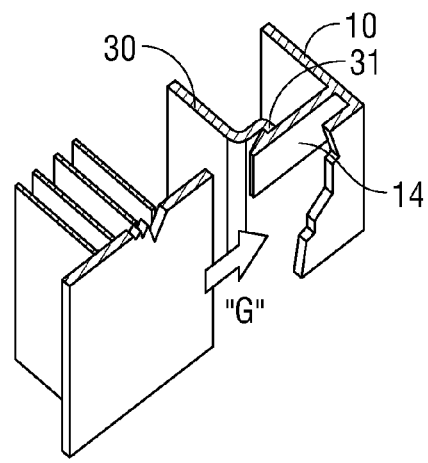
FIG. 13A   FIG. 13B
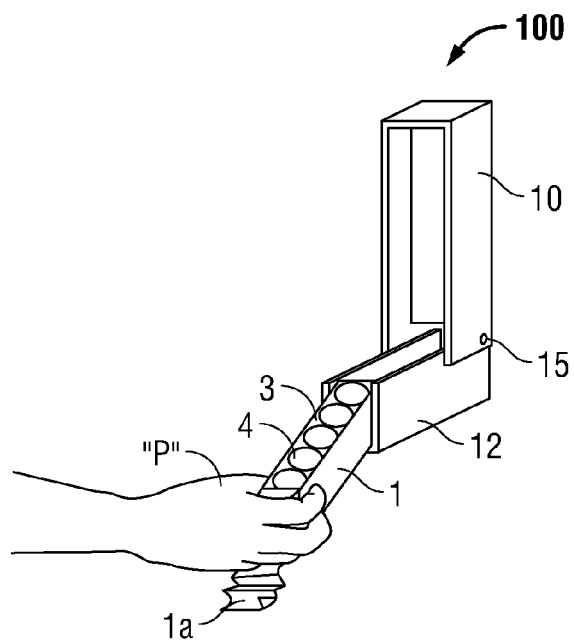
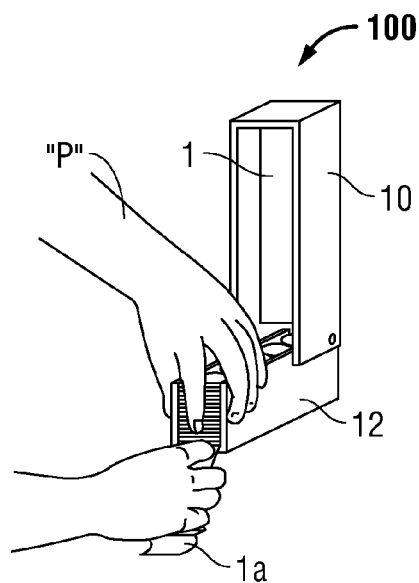
FIG. 14   FIG. 15

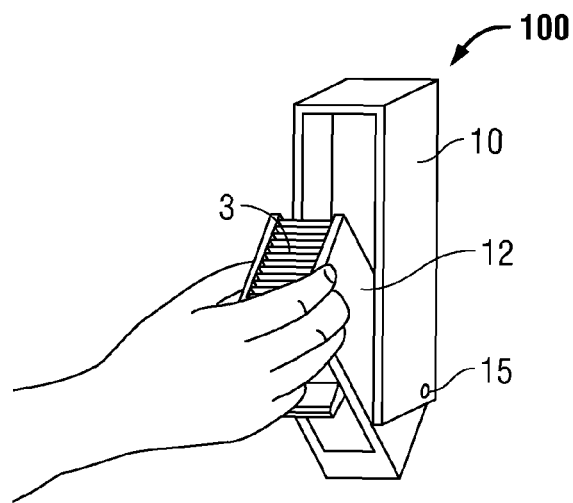
FIG. 16
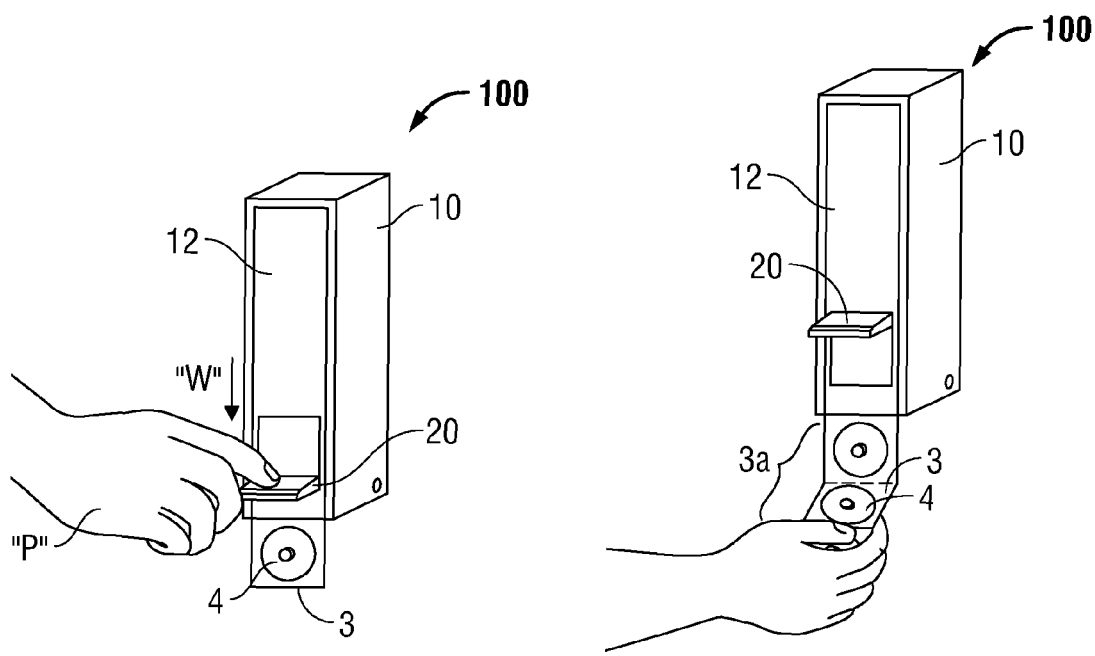
FIG. 17
FIG. 18

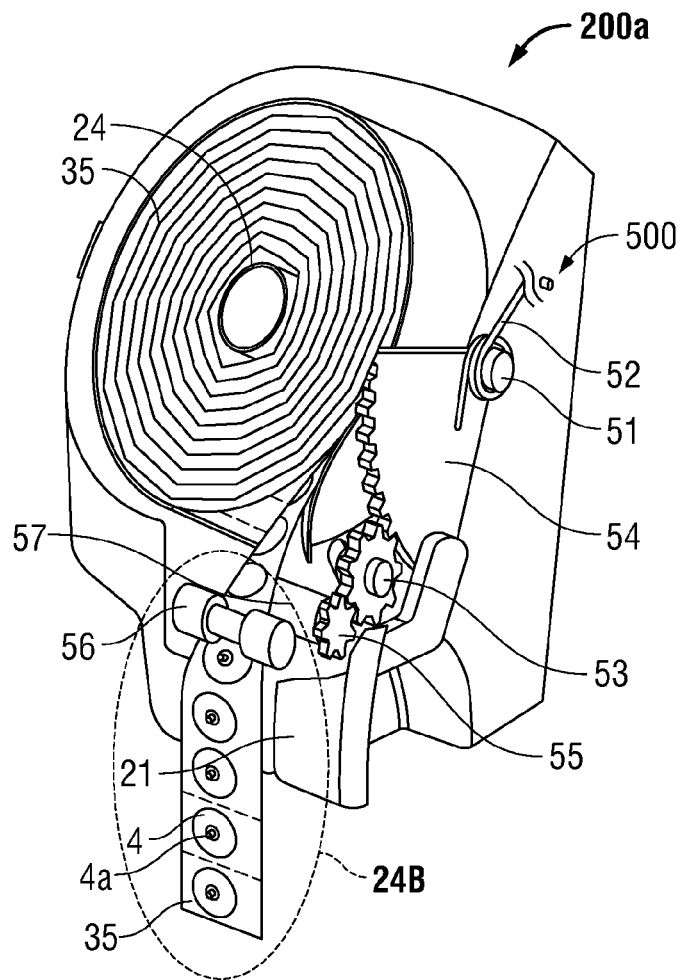
FIG. 24A
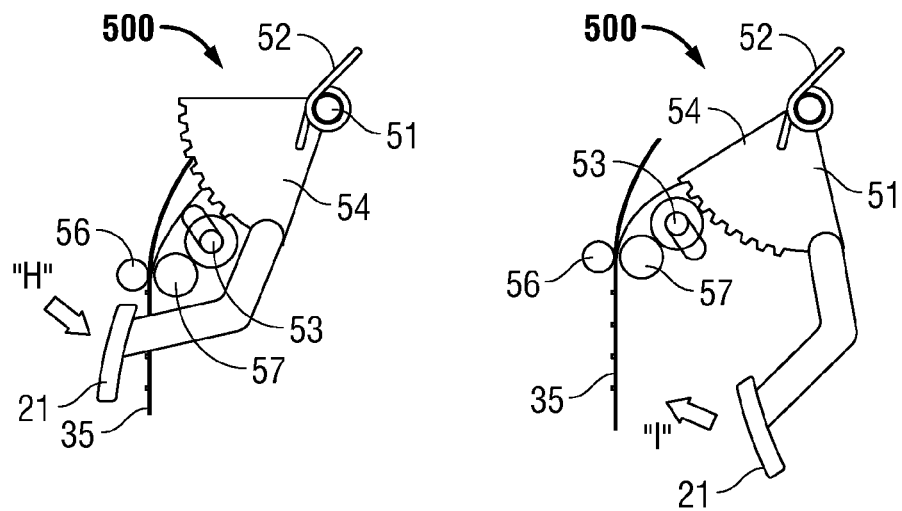
FIG. 24B   FIG. 24C

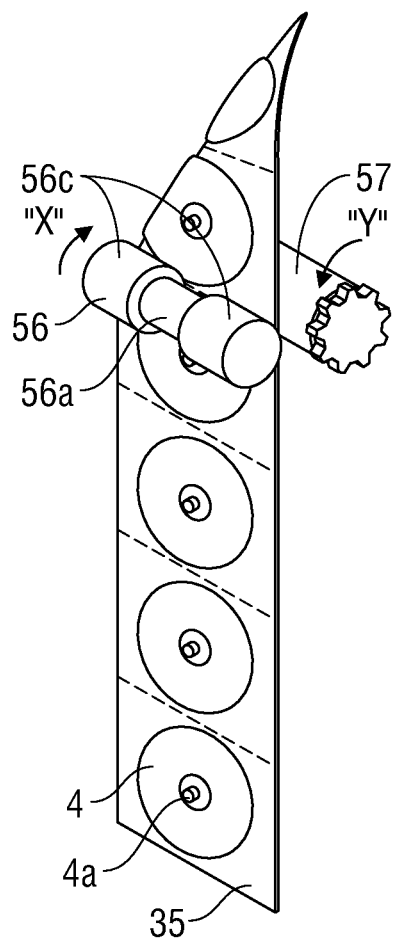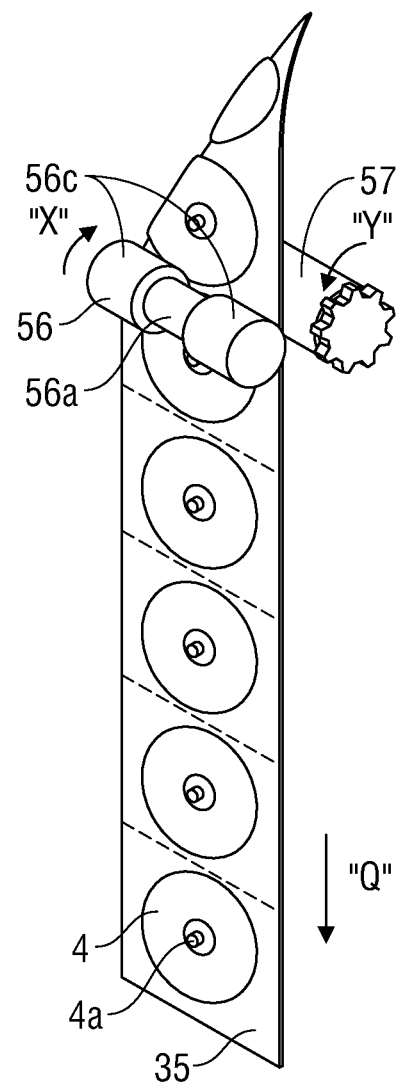
FIG. 24D  FIG. 24E

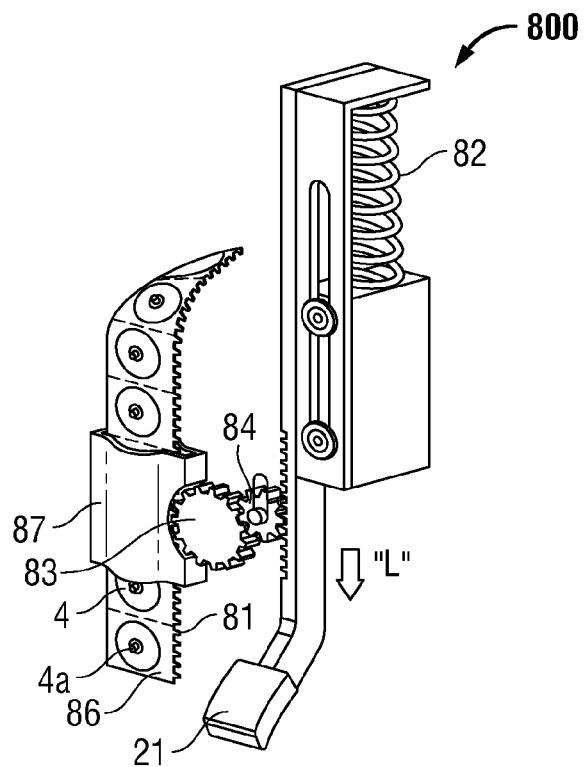
FIG. 27A
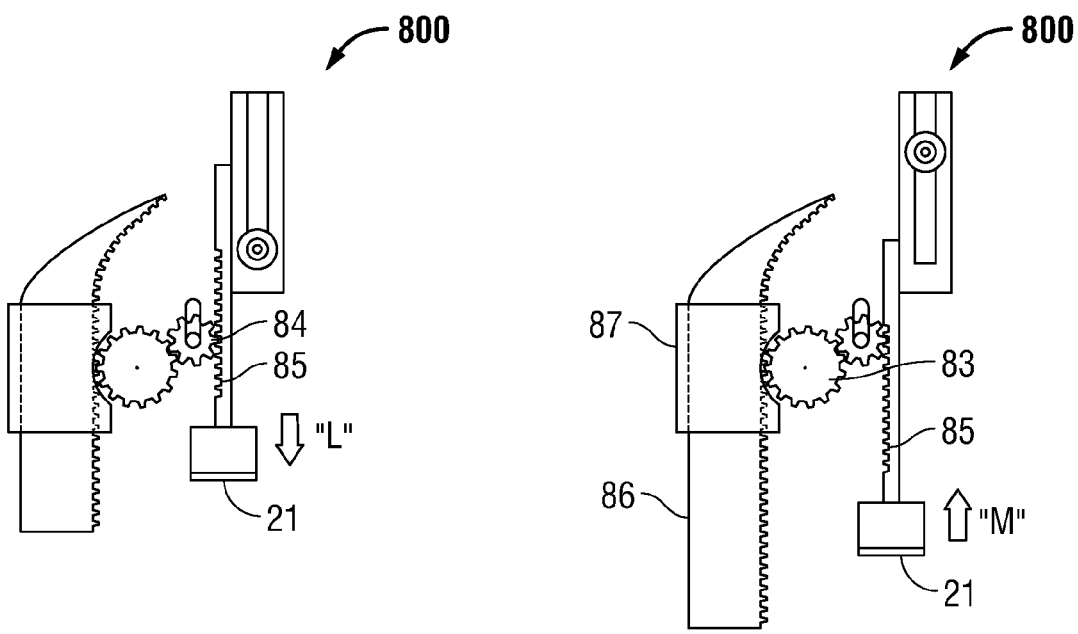
FIG. 27B
FIG. 27C

MEDICAL ELECTRODE DISPENSERS

CROSS-REFERENCE TO RELATED APPLICATION

The present application is an International Application claiming the benefit of and priority to U.S. Provisional Application Ser. No. 61/387,632, filed on Sep. 29, 2010, the entire content of which is incorporated herein by reference.

BACKGROUND

1. Technical Field

The present disclosure relates to dispensers for medical instruments, and more particularly, relates to dispensers adapted to dispense medical electrodes that are packaged in either strips or rolls.

2. Background of Related Art

Electrocardiography is concerned with the measurement and analysis of voltage potential readings taken from a limited number of anatomically defined locations. The voltages between various locations are combined to form electrocardiograph (ECG) leads that are represented as waveforms. ECG systems are generally used to detect or monitor abnormal heart rhythms, or arrhythmias, which arise from problems with the electrical conduction system of the heart. By recording the heart's electrical activity and comparing the recorded data with clinically developed criteria, the state of a person's heart can be diagnosed or classified.

ECG electrodes are applied to the skin of a patient in various locations and coupled to an ECG monitor. Both the number and placement of the electrodes are determined by established protocols dependent upon the information sought. For example, common protocols require the placement of electrodes in a 3-lead, a 5-lead, or a 12-lead configuration. Disposable ECG electrodes are used to inhibit the spread of disease among patients and to reduce sterilization costs. Accordingly, a need exists for dispensing ECG electrodes in a quick, efficient, and sterile manner such that clinicians can reduce the time associated with replacing ECG electrodes and the risk of contamination or the like.

SUMMARY

Accordingly, the present disclosure relates to a medical dispenser for storing and dispensing electrodes. The medical dispenser includes a housing having a front member and a back member, at least one electrode strip disposed between the front member and the back member of the housing and an actuator mounted to the front member of the housing and adapted to engage the at least one electrode strip. The electrode strip includes a strip member and a plurality of electrodes mounted to the strip member. The actuator is movable relative to the front member such that movement of the actuator results in corresponding movement of the at least one electrode strip to dispense an electrode from the housing. The actuator may be adapted to engage an electrode of the at least one electrode strip. In one embodiment, the actuator is adapted to engage a male terminal of the electrode.

The medical dispenser may include a plurality of electrodes strips arranged in superposed stacked relation and being disposed between the front member and the rear member of the housing. The front member and the back member may be adapted for relative movement and biased in a direction toward one another such that a front most electrode strip is biased against the front member. A biasing member may be positioned between the back plate and the housing. The biasing member is adapted to advance the back plate toward the front plate such that upon ejection of one of the electrode strips from the dispenser, the actuator engages an adjacent electrode strip. The front member of the housing may include a window to at least partially accommodate the male terminals within the window, The medical dispenser may include a cartridge for containing the plurality of electrode strips. The electrode strips disposed within the cartridge may be alternatively offset from one another such that male terminals of the electrodes of the adjacent electrode strips are alternatively coaxial with one of two axes. The cartridge housing may include an indicator window to provide visual indication of the number of electrodes remaining within the cartridge housing.

In another embodiment, the medical dispenser for storing and dispensing electrodes includes a housing having an outer wall defining a dispensing slot, a drum positioned within the housing, a strip of electrodes rolled about the drum and an actuator in operative engagement with the strip of electrodes. The strip of electrodes includes a strip member and a plurality of electrodes mounted to the strip member. The actuator is adapted to advance the strip of electrodes upon activation thereof to dispense an electrode through the dispensing slot of the housing. At least one roller may be operatively couplable with the actuator with the at least one roller configured and adapted to engage an electrode of the strip and dispense the electrode through the dispensing slot upon activation of the actuator. The at least one roller may be adapted to engage a male terminal of an electrode. A pair of rollers may be provided in juxtaposed relation with the strip of electrodes advancing though the pair of rollers upon activation of the actuator.

The medical dispenser may include a rack associated with the actuator and a gear associated with one of the rollers, whereby, upon activation of the actuator, the rack cooperates with the gear to cause rotation of the one roller and advancement of the strip of electrodes, to thereby dispense an electrode through the dispensing slot of the housing.

In an alternative embodiment, the medical dispenser includes a rack member associated with the actuator and at least one gear in operative engagement with the rack member, wherein upon activation of the actuator, the rack member cooperates to cause rotation of the at least one gear. In a further embodiment, the strip of electrodes include a grooved arrangement on an edge thereof. The at least one gear cooperates with the grooved arrangement to cause advancement of the strip of electrodes during activation of the actuator and corresponding rotation of the at least one gear.

These and other features of the current disclosure will be described in detail below with reference to the appended figures.

BRIEF DESCRIPTION OF THE DRAWINGS

Various embodiments of the present disclosure are described hereinbelow with reference to the drawings, wherein:

FIG. 5 is a side elevational view of a stack of electrodes;

FIG. 6 is a perspective view of an actuator of the electrode strip dispenser of FIG. 1;

FIG. 7A is a side view of the actuator of FIG. 6 shown in a first position;

FIG. 7B is a side view of the actuator of FIG. 6 shown in a second position;

FIG. 8 is a side cross-sectional, elevational view of the electrode strip dispenser of FIG. 1;

FIG. 9 illustrates the step of opening the container of FIGS. 2 and 3;

FIG. 10A illustrates the step of exposing the electrode strips within the container of FIGS. 2, 3, and 9;

FIG. 10B illustrates the opened container of FIGS. 2, 3, 9, and 10A;

FIG. 11 illustrates the step of unlocking the electrode strip dispenser of FIG. 1;

FIG. 12 illustrates the step of locking a spring loaded pusher plate against a housing the dispenser of FIG. 1;

FIG. 13A is a perspective view illustrating a latch for securing and releasing the spring loaded pusher plate of FIG. 12;

FIG. 13B is a perspective view illustrating the latch of FIG. 13A in a disengaged state;

FIG. 14 illustrates the step of loading the container of FIG. 3 into the electrode strip dispenser of FIG. 1;

FIG. 15 illustrates the step of securing the container of FIG. 3 within a portion of the electrode strip dispenser of FIG. 1;

FIG. 16 illustrates the step of closing the electrode strip dispenser of FIG. 1;

FIG. 17 illustrates the step of dispensing a length of electrode strip from the electrode strip dispenser of FIG. 1;

FIG. 18 illustrates the step of removing the length of electrode strip shown dispensed in FIG. 17;

FIG. 24A is a cutaway perspective view of the dispenser of FIG. 22 illustrating an actuator mechanism;

FIG. 24B is a side view of an actuator mechanism of FIG. 24A shown in a first condition;

FIG. 24C is a side view of the actuator mechanism of FIG. 24A shown in a second condition;

FIG. 24D is an enlarged view of the indicated area of detail shown in FIG. 24A illustrated in a first condition;

FIG. 24E is the indicated area of detail of FIG. 24A as shown in FIG. 24D illustrated in a second condition;

FIG. 27A is a perspective view of a further embodiment of an actuator mechanism;

FIG. 27B is a side view of the actuator mechanism of FIG. 27A shown in a first condition;

FIG. 27C is a side view of the actuator mechanism of FIG. 27A shown in a second condition;

DETAILED DESCRIPTION OF THE EMBODIMENTS

Figure 1:
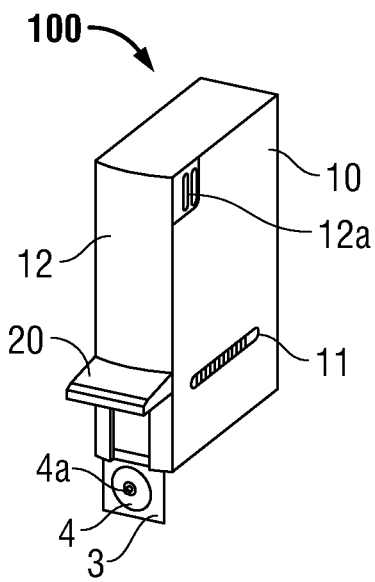
FIG. 1 is a perspective view of an electrode strip dispenser in accordance with an embodiment of the present disclosure.

In the figures and in the description that follows, in which like reference numerals identify similar or identical elements, the term "proximal" will refer to the end of the device that is closer to the physician, while the term "distal" will refer to the end that is farther from the clinician.

A dispenser 100 for dispensing medical objects, e.g., a strip of electrodes, will now be described with reference to FIGS. 1-18. Dispenser 100 is configured and adapted to dispense electrode strips 3. Each electrode strip 3 stores at least one electrode 4 and may include a plurality of electrodes 4, e.g., five electrodes arranged in a single row on a single backing or strip member 3a. Within the dispenser 100, the electrode strips 3A are arranged in superposed stacked relation. A stack 5 of strips 3 may be stored, prior to use, within a container 1. Each strip 3 may be offset from an adjacent strip 3 such that snaps 4a of electrodes 4 are alternatively coaxial with one of an axis A and an axis B, as shown in FIG. 5.

Figure 2:
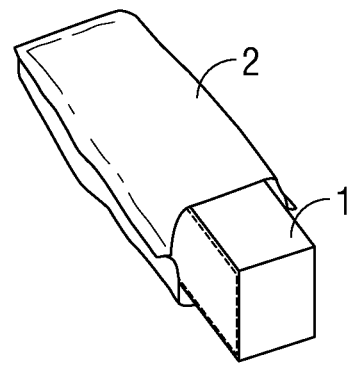
FIG. 2 is a perspective view of a container for storing a plurality of electrode strips arranged in one or more stacks and adapted to be loaded into the electrode strip dispenser of FIG. 1 shown partially inserted within a packaging.
Figure 3:
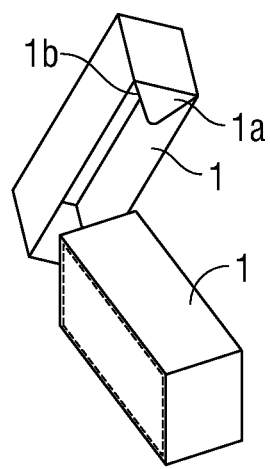
FIG. 3 is a perspective view of the container of FIG. 2 shown removed from the packaging.

As seen in FIGS. 2 and 3, the stack 5 of strips 3 may be stored prior to use within a container 1 that may be packaged within packaging 2, e.g., a foil package. Container 1 is adapted and configured to be loaded in its entirety into the dispenser 100 such that strips 3 will remain housed within the container 1 until being dispensed. A seal 1a, defined by a perforation 1b in the container 1, facilitates opening of the container 1. As shown in FIGS. 9-11, prior to insertion of the container 1 into the dispenser 100, the seal 1a is peeled back or removed to expose the electrode strips 3 stored therein.

Figure 4:
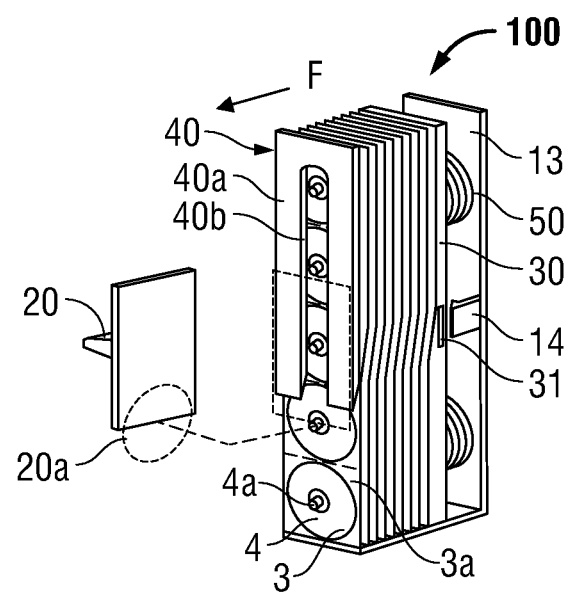
FIG. 4 is a perspective view of the electrode strip dispenser of FIG. 1, partially separated and shown with a housing removed and loaded with a stack of electrode strips.

As best depicted in FIGS. 4 and 8, dispenser 100 includes a back member or pusher plate 30 that is disposed in housing 10 for advancing the stack 5 of strips 3, or the entire container 1 storing the stack 5 therein. The pusher plate 30 may be advanced by at least one spring 50, e.g., a coil spring. A pair of springs 50 may be positioned between pusher plate 30 and housing 10 to provide a constant force in the direction of arrow "F" toward a front plate 40 of the dispenser 100.

Springs 50 may be positioned at or near upper and lower portions of the pusher plate 30.

Dispenser 100 also includes an actuator 20 positioned on an outer surface 40a of front plate 40 and is configured and adapted to engage a top or front most strip of the stack 5 of strips 3. A distal end 20a of actuator 20 is configured and adapted to engage male terminals or snaps 4a of electrodes 4 such that translation of actuator 20, relative to front plate 40 and/or housing 10, e.g., in the direction indicated by arrow "D" (FIGS. 6, 7A, and 7B), results in translation of the strip 4 and ejection of the strip 4 or a portion of the strip 4 from the dispenser 100. The front plate 40 includes a window or cutout portion 40b (FIG. 4) configured and adapted to accommodate snaps 40a of electrodes 4 such that the electrodes 4 may be pressed against the front plate 40 in a substantially flat manner and inhibiting swaying or rocking of the electrodes 4.

As discussed above, pusher plate 40 is under a constant force, in the direction of arrow "F" toward the front plate 40 (FIG. 4), such that as one strip 3, e.g., a front most or first strip, is ejected from the dispenser 100, another adjacent strip 3 is advanced to engage actuator 20. In particular, as seen in FIGS. 6, 17, and 18, once the strip 3 is advanced at least the length of one electrode 4, a biasing member or a spring 60 translates actuator 20 in the direction of arrow "C", such that actuator 20 returns to its initial un-actuated position. Biasing member or spring 60 may be secured to actuator 20 and, e.g., front plate 40 in a manner appreciated by one skilled in the art. Once a portion or length 3a of the strip 3 is exposed or dispensed, the entire remaining, un-dispensed portion or length of the strip 3 may be removed manually from dispenser 100. Removal of a strip 3 results in the advancement of a new strip 3 to be engaged by actuator 20. Alternatively, the exposed or dispensed portion or length 3a of the strip 3 may be cut or torn from the rest of the strip 3.

With reference to FIG. 11, loading dispenser 100 with electrode strips 3 is accomplished by a clinician "P" opening the dispenser by holding the grip 12a and moving the hopper in the direction indicated by arrow "V". After opening the dispenser, the clinician "P" translates a pusher plate 30 in a direction indicated by arrow "G" (FIG. 12) to secure the pusher plate 30 behind a latch 14 extending from the housing 10, as seen in FIG. 13B. As seen in FIGS. 4, 8, 13A, and 13B, moving the pusher plate in direction "G" and behind a latch 14, secures a lip 31 of the pusher plate 30 behind the latch 14 to facilitate loading the container 1. It is to be noted that upon closing the hopper 12, the latch 14 will disengage from the pusher plate 30, as seen in FIG. 13A. Once the pusher plate 30 is secured as described above, the clinician "P" loads the container 1 into the hopper 12, as shown in FIGS. 14-15, and closes the hopper 12 as shown in FIG. 16. Actuator 20 may now be translated in the direction indicated by arrow "W" to dispense the electrode strip 30, as shown in FIG. 17. A length 3a of the electrode strip 3 may now be removed from the dispenser 100, as shown in FIG. 18.

Figure 20:
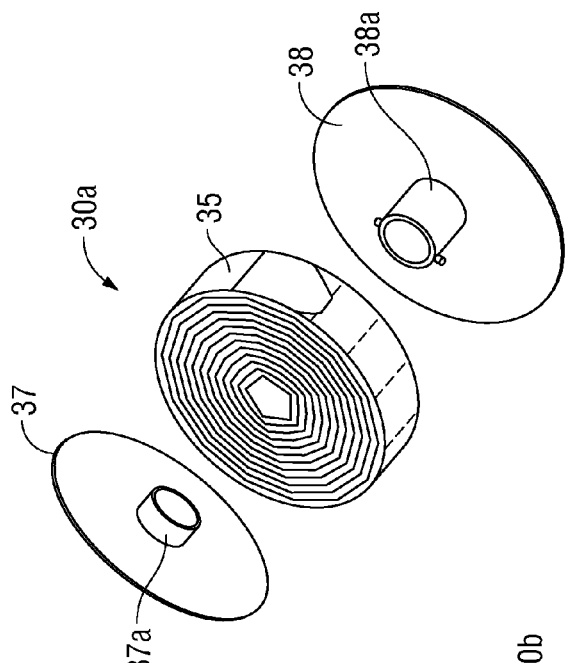
FIG. 20 is an exploded perspective view of the spool of FIG. 19.
Figure 21:
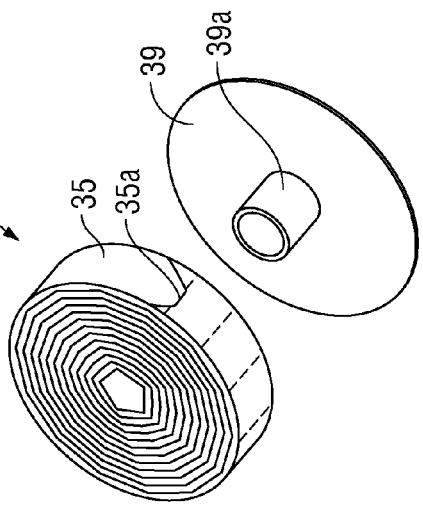
FIG. 21 is an exploded perspective view of another embodiment of a spool.

In accordance with another embodiment, dispensers that are configured and adapted to dispense electrodes from a roll will now be described with reference to FIGS. 19-37. A spool 30a, for use in a dispenser, includes a rolled strip 35 of electrodes 4. As shown in FIG. 20, spool 30a includes two backers 37, 38 that are configured and adapted to be secured together. The two backers 37, 38 when secured together define a tube that stabilizes the rolled strip 35 as the rolled strip 35 is advanced through the dispenser. In an alternative embodiment, shown in FIG. 21, a spool 30b may include a backer 39 that provides a surface for the clinician "P" to grasp and handle. A post 39a, extending from the backer 39, stabilizes the rolled strip 35 and inhibits deformation of the electrodes 4 stored thereon.

Figure 19:
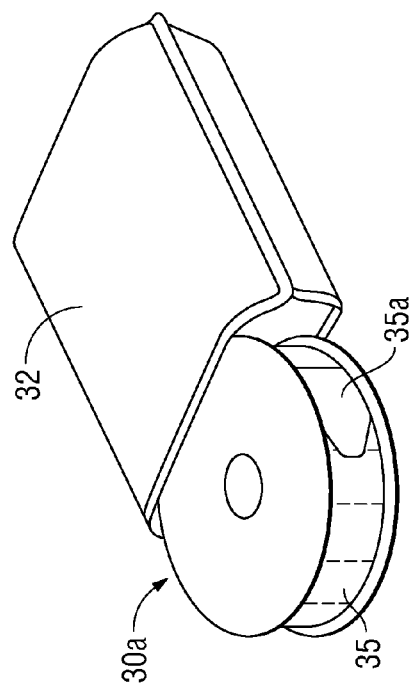
FIG. 19 is a perspective view of a spool wound with a length of a strip of electrodes and a package for storing the spool in accordance with another embodiment of the present disclosure.

As seen in FIG. 19, spool 30a may be stored in a packaging 32, e.g., a pouch or a foil wrapper, prior to use to facilitate long-term storage. Packaging 32 may also be used to store spool 30b. By packaging a large number of electrodes 4, the amount of waste is less per electrode 4 than it would be for a package containing fewer electrodes.

FIGS. 22 to 36 illustrate dispensers configured and adapted to dispense electrodes 4 stored within spools 30a, 30b. While the dispensers illustrated in FIGS. 22-36 are shown in use with spool 30b, it is to be understood that operation of the dispensers with spool 30a would be substantially the same as described below with reference to spool 30b. Dispenser 200a of FIG. 22 includes a manual drive mechanism and is a configured and adapted to dispense electrodes 4 from either spool 30a or spool 30b. Dispenser 200a includes a housing 22 and a drum 24 that is configured and adapted to receive either spool 30a or spool 30b thereon. Upon actuation of a manual actuator 21, e.g., a handle, a length of strip 35 is dispensed from a slot 23 within housing 22.

Figure 23:
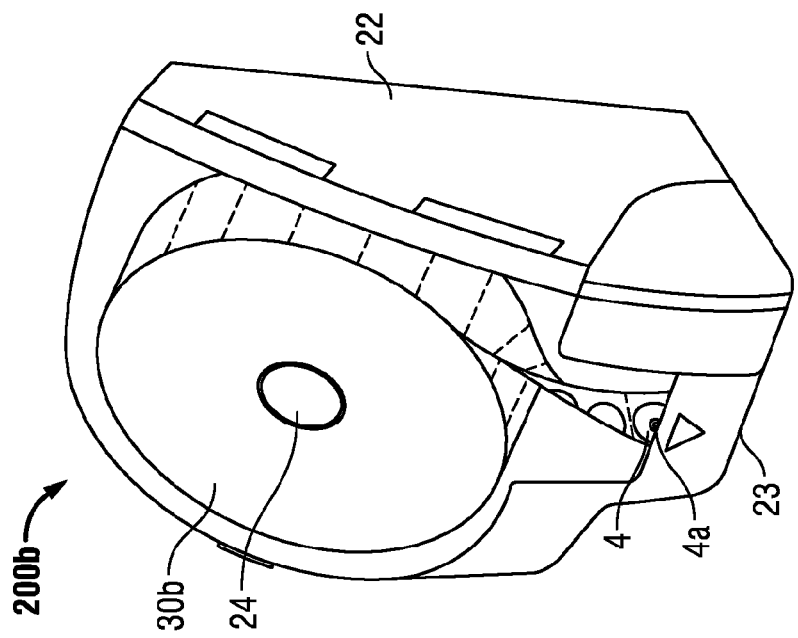
FIG. 23 is a perspective view depicting an alternate embodiment of the strip dispenser of FIG. 22.
Figure 22:
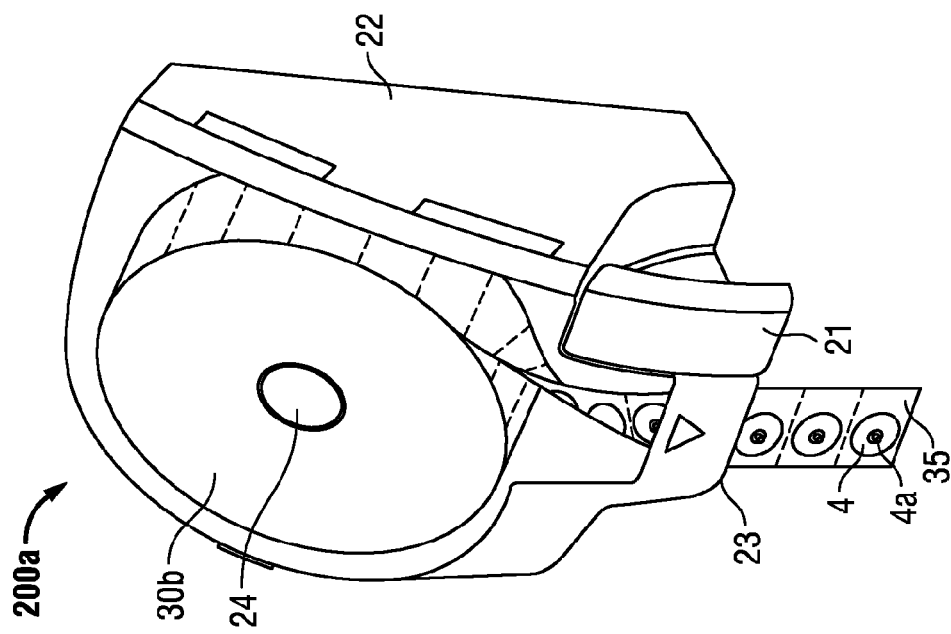
FIG. 22 is a perspective view depicting another embodiment of a strip dispenser in accordance with the present disclosure.

Dispenser 200b, shown in FIG. 23, is substantially similar to dispenser 200a but may be an automatic dispenser that ejects a length or portion of strip 35 in response to an activation stimulus, e.g., a sensor may detect movement or a voice command.

Different embodiments of drive mechanisms coupled to a manual actuator will now be described with reference to FIGS. 24-27C. It is to be understood that, while these drive mechanisms are coupled to a manual actuator, the drive mechanisms described below may be coupled to a motor and may be employed by the dispenser 200b, previously described.

As seen in FIGS. 24, 24B, 24C, drive mechanism 500 of dispenser 200a includes a manual actuator 21, e.g., a handle, operatively coupled to a rack 54 that is biased toward an initial position in a direction indicated by arrow "I" (FIG. 24C) by a spring 52 that is coupled to hub 51 extending from a surface of the rack 54. Spring 52 may be a torsion spring secured to a side wall of the dispenser 200a and to the rack 54 by conventional means. Rack 54 interacts with a first spur gear 53 that engages with a second spur gear 55. Second spur gear 55 is coupled to a first roller 57 which is arranged about the same axis of the second spur gear 55.

Dispenser 200a is configured and adapted to advance strip 35 in one direction, upon actuation of manual actuator 21 in the direction indicated by arrow "H" (FIG. 24A). Upon ejecting or dispensing a length of strip 35, manual actuator 21 returns to its initial position, in the direction indicated by arrow "I", without advancing or changing the position of the strip 35. As shown best in FIGS. 24D and 24E, the first roller 57 is in a juxtaposed and parallel relation with a second roller 56. In one embodiment, the first roller 57 engages end members 56c of second roller 56 such that rotation of first roller 57 results in rotation of second roller 56. In another embodiment, first roller 57 and second roller 56 engage the rolled strip 35 in a frictional relation to cause simultaneous movement of the rollers 56, 57. The rolled strip 35 of electrodes 4 is placed between the rollers 56, 57 in a frictional relationship such that as rollers 56, 57 rotate in the direction shown by arrows "X", "Y", respectively, the strip 35 translates in the direction indicated by arrow "Q". The second roller 56 includes an axle 56 that provides a space to inhibit interference between snaps 4a of electrodes 4 and the roller 56 as the strip 35 translates.

Figure 25A:
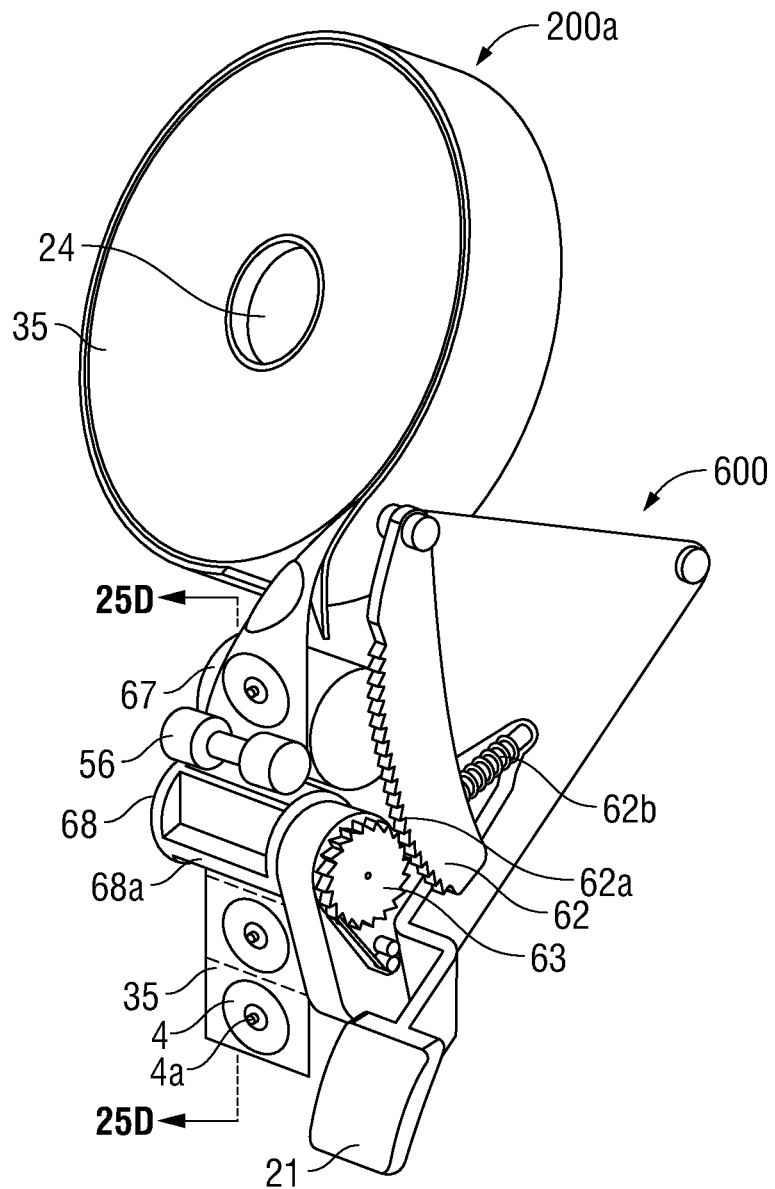
FIG. 25A is a cutaway perspective view of the dispenser of FIG. 22 illustrating another embodiment of an actuator mechanism.
Figure 25B:
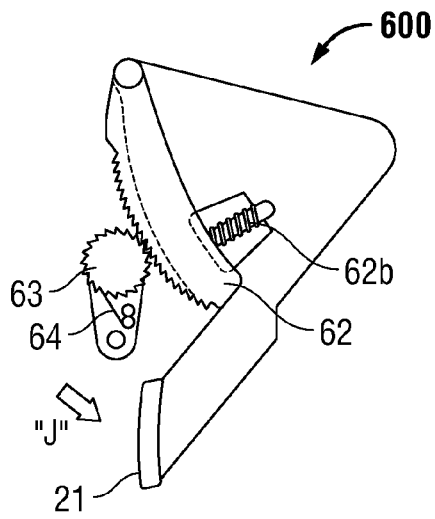
FIG. 25B is a side view of the actuator mechanism of FIG. 25A shown in a first condition.
Figure 25C:
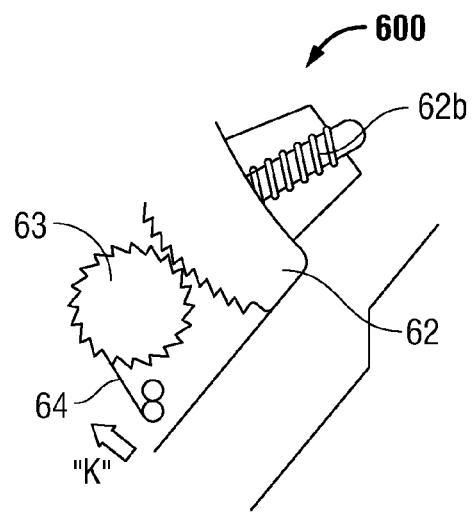
FIG. 25C is a side view of the actuator mechanism of FIG. 25A shown in a second condition.
Figure 25D:
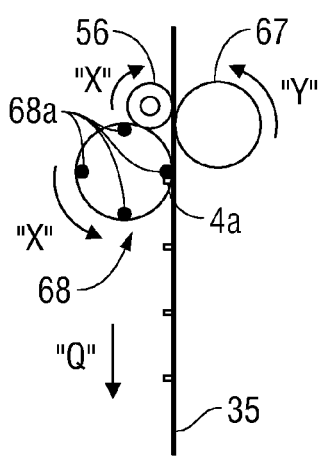
FIG. 25D is a side view of the indicated area of FIG. 25A taken along section line 25D-25D.

In another embodiment, as seen in FIGS. 25A-25D, drive mechanism 600 includes a rack 62 that is operatively coupled to a spring 62b, which is adapted to facilitate repositioning of the rack 62. Rack 62 is operatively coupled to a spur gear 63, which is coaxially mounted to roller 68. Spur gear 63 is biased to rotate in one direction by a spring or biasing member 64. Both the rack 62 and the spur gear 63 include angled teeth 62a, 63a, respectively. In the initial position, the rack 62 engages gear 63 and inhibits rotation of the gear 63. As the manual actuator 21 is depressed in the direction indicated by arrow "J" (FIG. 25B), the rack gear 62 is retracted and displaced from the spur gear 63 with the spur gear 63 released from rack 62, the spring or biasing member 64 will cause rotation of the spur gear 63, which in turn causes rotation of roller 68. Roller 68 includes a plurality of splines 68a. As roller 68 rotates, the splines 68a engage one or both of rollers 56, 67. The rollers 56, 67, 68 are in contact with one another such that rotation of one of the rollers 56, 67, 68 effects rotation of the other two rollers. The rollers 56, 67 are in a juxtaposed relationship and compress strip 35 therebetween such that rotation of rollers 56, 67 effects translation of the strip 35. In addition, as shown in FIGS. 25A and 25D, the splines 68a of the roller 68 are adapted to engage snaps 4a of the electrodes 4 such that as roller 68 rotates in the direction indicated by arrow "X", the strip 35, to which electrodes 4 are affixed, translates in the direction indicated by arrow "Q". Accordingly, depression of the manual actuator 21 results in dispensing of a length of the strip 35. Upon completion of the sequence described above, the manual actuator 21 returns to its initial position in the direction indicated by arrow "K". With the manual actuator 21 returned to the initial position, the rack 62 engages gear 63 and inhibits rotation of gear 63.

Figure 26:
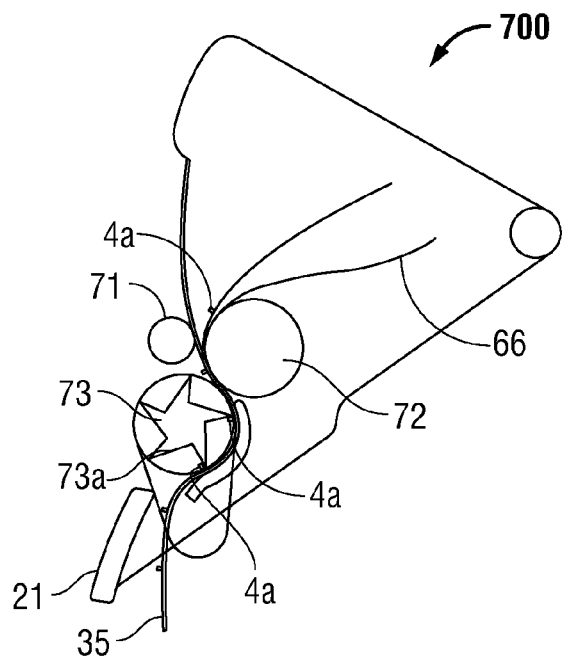
FIG. 26 is a side view of yet another actuator mechanism.

In yet another embodiment, as shown in FIG. 26, drive mechanism 700 includes rollers 71, 72, which are adapted to lead strip 35 therethrough and to stabilize the strip 35. A band 66 capable of small deflections is engaged with manual actuator 21 to bias the manual actuator 21 toward its initial position. Activation of the manual actuator 21 results in the rotation of a roller 73. Roller 73 includes a plurality of fingers 73a that are radially spaced apart to engage snaps 4a of electrodes 4 such that rotation of roller 73 effects translation of the strip 35.

An alternate drive mechanism 800 will now be described with reference to FIGS. 27A-27C. Drive mechanism 900 includes a manual actuator 21 that is coupled to a biasing member 82, e.g., in the form of a helical spring, that biases manual actuator 21 to an initial position in the direction of arrow "M" (FIG. 27C). Manual actuator 21 supports a gear rack 85 that engages a first spur gear 84 that is operatively coupled to a second spur gear 83 that is configured and adapted to engage a plurality of equidistantly spaced notches or grooves 81 along a side of a strip 86 of electrodes 4. Strip 86 may be rolled into a spool and loaded into the dispensers in a substantially similar manner as already described with reference to spools 30a, 30b. In use, movement or translation of manual actuator 21, in the direction indicated by arrow "L" (FIG. 27B), results in the ultimate rotation of second spur gear 83 and the translation of strip 86. A collar 87 may be provided, through which strip 86 passes, in order to facilitate interaction between the second spur gear 83 and the strip 86.

Figure 28:
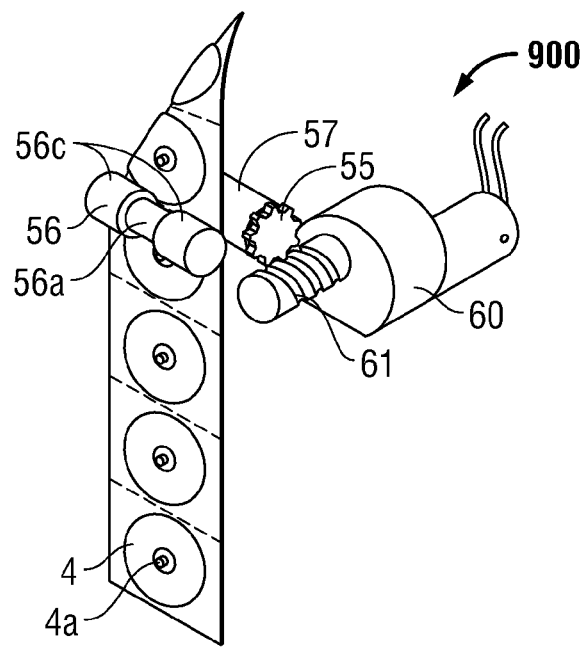
FIG. 28 is a perspective view of still another actuator mechanism in accordance with the present disclosure.
Figure 29:
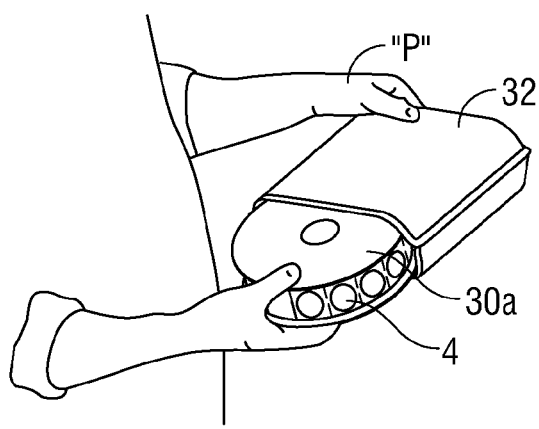
FIG. 29 illustrates the step of removing the spool of FIG. 19 from the packaging of FIG. 19.
Figure 30:
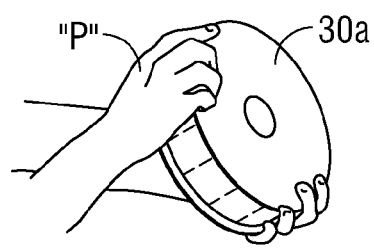
FIG. 30 illustrates the step of removing the outer banding of the spool of FIG. 19.

A motorized drive mechanism 900 will now be described with reference to FIG. 28. Rollers 56, 57 are adapted to receive strip 35 therebetween, as described above with reference to FIG. 24D-24E. Drive mechanism 900 includes an electric motor 60 that rotates a worm gear 61. Worm gear 61 engages spur gear 55, which is operatively coupled to roller 57 to effect rotation thereof. Rotation of roller 57 results in the rotation of roller 56. As described above, as roller 56 rotates, roller 56 engages snaps 4a of electrodes 4, resulting in the advancement of strip 35.

An exemplary method of loading spool 30a into manual dispenser 200a will now be described with reference to FIGS. 29-36. It will be understood that handling of spool 30b is substantially similar to that of spool 30a and will therefore not be discussed in detail herein. It will also be understood the steps loading of spools 30a, 30b into automatic dispenser 200b is substantially similar to that described with respect to manual dispenser 200a. The method of loading spools 30a, 30b differs between dispenser 200a and dispenser 200b in that dispenser 200b does not require manual advancement of spool 30a, 30b.

Figure 32:
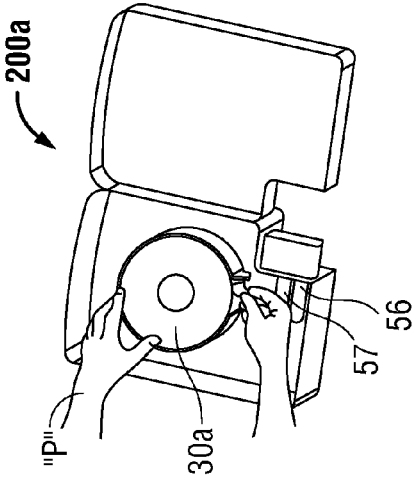
FIG. 32 illustrates the step of preparing the spool of FIG. 19 for use after placing the spool into the dispenser of FIG. 22.
Figure 31:
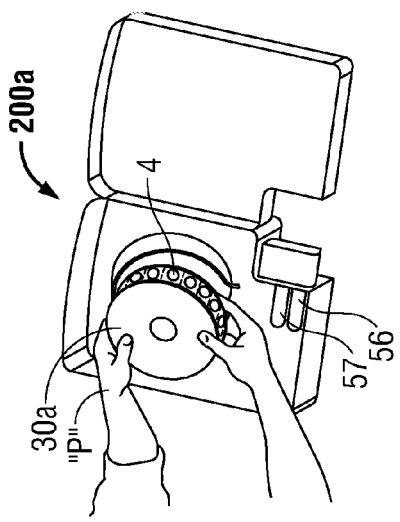
FIG. 31 illustrates the step of inserting the spool of FIG. 19 into the dispenser of FIG. 22.
Figure 34:
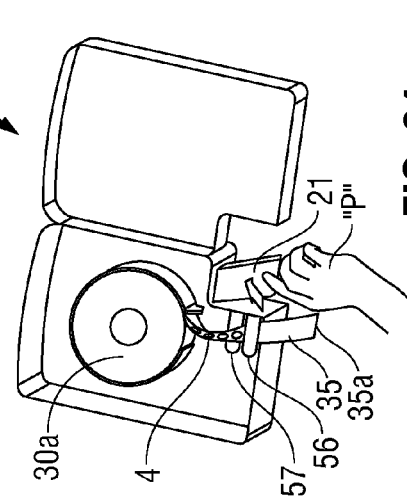
FIG. 34 illustrates the step of advancing the spool of FIG. 19 in the dispenser of FIG. 22.
Figure 33:
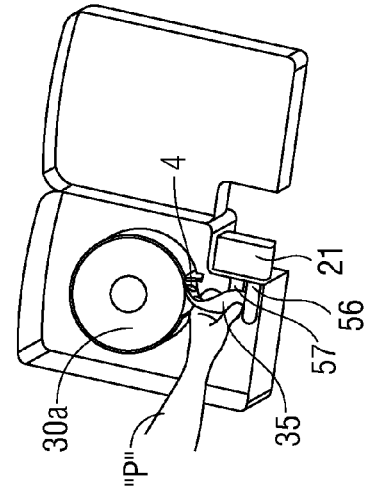
FIG. 33 illustrates the step of feeding a starter tab of the spool of FIG. 19 between rollers of the dispenser of FIG. 22.
Figure 35:
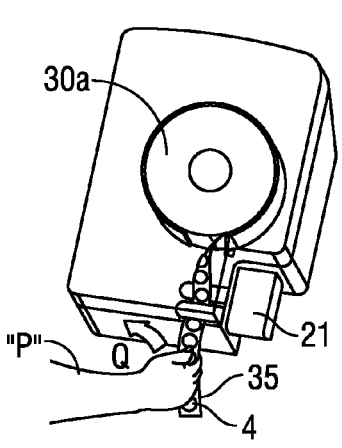
FIG. 35 illustrates the step of dispensing electrodes from the dispenser of FIG. 22.
Figure 36:
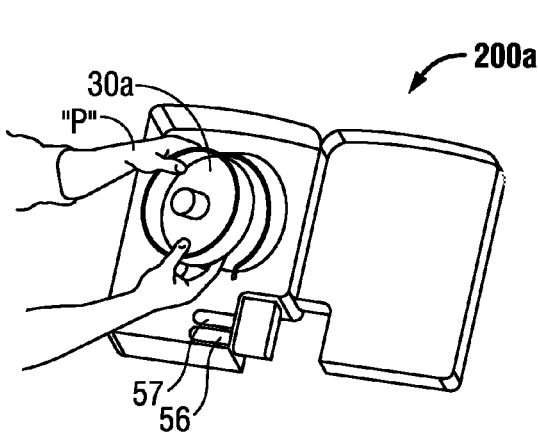
FIG. 36 illustrates the step of removing the spool of FIG. 19 from the dispenser of FIG. 22.

In particular, clinician "P" removes spool 30a from packaging 32 (see FIG. 29), and then ensures a proper orientation of the spool 30a (see FIG. 30), and then places the spool 30a within dispenser 200a (see FIG. 31). As shown in FIGS. 32-33, after inserting the spool 30a into the dispenser 200a, the clinician "P" leads a portion or tip 35a of strip 35 through rollers 56, 57 and further advances the strip by depressing manual actuator 21, e.g., a handle (see FIG. 34). The initial portion of the strip 35 that is passed through rollers 56, 57 may be torn away from the remainder of the strip 35 by tearing the strip 35 along directional arrow "Q" (see FIG. 35). Moreover, after dispensing a length of strip 35, including electrodes 4, the dispensed strip 35 is torn from the remaining rolled strip 35. Removal of the used spool 301 is shown in FIG. 36.

Figure 37:
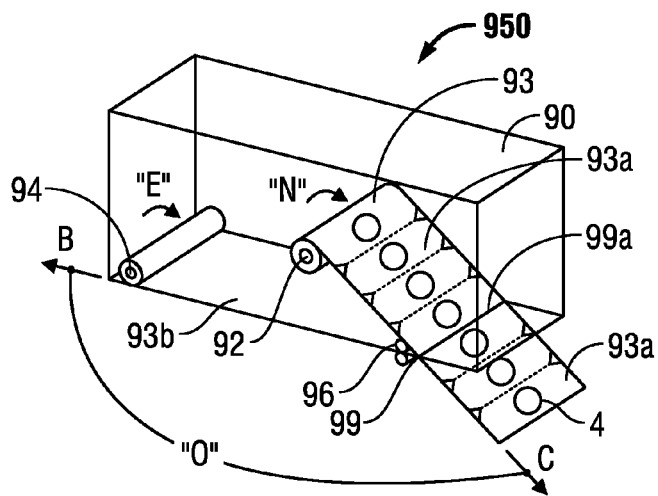
FIG. 37 illustrates another embodiment of a dispenser.

Turning now to FIG. 37, a dispenser according to another embodiment of the present disclosure will now be described. A dispenser 950 is adapted to store a strip 93 of electrodes 4. The strip 93 includes a backing 93a to which electrodes 4 are affixed and a release liner 93b to which the backing 93a is coupled. As the strip 93 is advanced, the backing 93a along with electrodes 4 are dispensed from the dispenser 950 while the release liner 93b is stored within the dispenser 950. As shown in FIG. 37, line segment OB is coplanar with the surface defined by release liner 93b and line segment OC is coplanar with the surface defined by backing 93a. The greater the angle "BOC" or "θ" between the surface defined by the backing 93a and the release liner 93b, the more readily the release liner 93b will separate from the backing 93a. In some embodiments, the angle "θ" may be between 90° and 180°. In other embodiments, the angle "θ" may be between 150° and 180°. Advancement of the strip 93 out through slot 99 results in rotation of the roller 93 in the direction indicated by arrow "N" and the strip 93 separates into two parts: the backing 93a along with electrode 4 and the release liner 93b. A peel bar 99a positioned at or near the slot 99 may facilitate release of the electrodes 4 from backing 91. A cam actuation may facilitate advancement of the next electrode 4 subsequent to dispensing of an electrode. Alternatively, a trigger mechanism may be utilized to force the next electrode 4 into position. The self release mechanism described above may facilitate direct application of electrodes 4 to a patient akin. In an embodiment, a cam actuation may automatically advance the strip 93 after dispensing an electrode 4. In addition, the strip 93 includes an indexing function to ensure proper alignment of the electrodes 4 with the housing 90. The release liner 93b may be fed to a take-up roller 94, which may be manually or automatically actuated.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A medical dispenser for storing and dispensing electrodes, which comprises:
a housing including a front member and a back member;
at least one electrode strip disposed between the front member and the back member of the housing, the electrode strip including a strip member and a plurality of electrodes mounted to the strip member; and
an actuator positioned on the front member of the housing and adapted to engage a male terminal of at least one of the plurality of electrodes, the actuator movable relative to the front member such that movement of the actuator results in corresponding movement of the at least one electrode strip to dispense an electrode from the housing.

2. The medical dispenser according to claim 1 including a plurality of electrode strips arranged in superposed stacked relation and being disposed between the front member and the back member of the housing.

3. The medical dispenser according to claim 2 wherein the front member and the back member are adapted for relative movement and are biased in a direction toward one another such that a front most electrode strip is biased against the front member.

4. The medical dispenser according to claim 2 further comprising a biasing member positioned between the back member and the housing, the biasing member adapted to advance the back member toward the front member such that upon ejection of one of the electrode strips from the dispenser, the actuator engages an adjacent electrode strip.

5. The medical dispenser according to claim 2 wherein the front member includes a window, the male terminals of the front most strip at least partially accommodated within the window.

6. The medical dispenser according to claim 2 wherein the male terminals of the electrodes of adjacent electrode strips are alternatively offset from one another.

7. The medical dispenser according to claim 2, further comprising a cartridge for containing the plurality of electrode strips.

8. The medical dispenser according to claim 7 wherein the electrode strips disposed within the cartridge are alternatively offset from one another such that male terminals on the electrodes, included within the electrode strips, are alternatively coaxial with one of two axes.

9. The medical dispenser according to claim 7, wherein the cartridge housing includes an indicator window to provide visual indication of the number of electrodes remaining within the cartridge housing.

10. A medical dispenser for storing and dispensing electrodes, which comprises:
a housing including:
a front member having an opening to dispense electrodes; and
a back member;
a plurality of electrode strips arranged in superposed stacked relation and being disposed between the front member and the back member of the housing, at least one of the plurality of electrode strips including a strip member and a plurality of electrodes mounted to the strip member; and
an actuator positioned on the front member of the housing to engage an electrode of the at least one electrode strip, wherein the actuator is movable relative to the front member such that movement of the actuator from a first position to a second position results in corresponding movement of the electrode to dispense an electrode through the front member opening.

11. The medical dispenser according to claim 10 wherein the actuator is positioned on an outer surface of the front member.

12. The medical dispenser according to claim 10 further comprising an actuator biasing member to return the actuator to the first position.

13. The medical dispenser according to claim 10 wherein the front member and the back member are adapted for relative movement and are biased in a direction toward one another such that a front most electrode strip is biased against the front member.

14. The medical dispenser according to claim 10 further comprising a biasing member positioned between the back member and the housing, the biasing member adapted to advance the back member toward the front member such that upon ejection of one of the electrode strips through the front member opening, the actuator engages an adjacent electrode strip.

15. The medical dispenser according to claim 10 wherein the front member includes a window, the male terminals of the front most strip at least partially accommodated within the window.

16. The medical dispenser according to claim 10 wherein the male terminals of the electrodes of adjacent electrode strips are alternatively offset from one another.

17. The medical dispenser according to claim 10, further comprising a cartridge for containing the plurality of electrode strips.

18. The medical dispenser according to claim 17 wherein the electrode strips disposed within the cartridge are alternatively offset from one another such that male terminals on the electrodes, included within the electrode strips, are alternatively coaxial with one of two axes.

19. The medical dispenser according to claim 17, wherein the cartridge housing includes an indicator window to provide visual indication of the number of electrodes remaining within the cartridge housing.

* * * * *